(12) United States Patent
King

(10) Patent No.: US 12,364,847 B2
(45) Date of Patent: Jul. 22, 2025

(54) VALVE COMPONENT AND VALVE ASSEMBLY

(71) Applicant: VASCUTEK LIMITED, Strathclyde (GB)

(72) Inventor: John King, Strathclyde (GB)

(73) Assignee: Vascutek Limited, Renfrewshire (GB)

(*) Notice: Subject to any disclaimer, the term of this patent is extended or adjusted under 35 U.S.C. 154(b) by 1057 days.

(21) Appl. No.: 17/264,135

(22) PCT Filed: Jul. 30, 2019

(86) PCT No.: PCT/GB2019/052130
§ 371 (c)(1),
(2) Date: Jan. 28, 2021

(87) PCT Pub. No.: WO2020/025945
PCT Pub. Date: Feb. 6, 2020

(65) Prior Publication Data
US 2021/0299424 A1    Sep. 30, 2021

(30) Foreign Application Priority Data
Jul. 30, 2018 (GB) .................. 1812367

(51) Int. Cl.
*A61M 39/06* (2006.01)
*A61M 39/00* (2006.01)

(52) U.S. Cl.
CPC ..... *A61M 39/06* (2013.01); *A61M 2039/0036* (2013.01); *A61M 2039/062* (2013.01); *A61M 2039/066* (2013.01)

(58) Field of Classification Search
CPC .. A61M 2039/06646; A61M 2309/062; A61M 36/06; A61M 39/0606;
(Continued)

(56) References Cited

U.S. PATENT DOCUMENTS 4,798,594 A    1/1989    Hillstead
4,895,565 A    1/1990    Hillstead
(Continued)

FOREIGN PATENT DOCUMENTS

EP        0369314 A2     5/1990
JP        H07148265 A    6/1995
(Continued)

OTHER PUBLICATIONS

International Search Report and Written Opinion of the International Searching Authority for International Application No. PCT/GB2019/052130 mailed on Nov. 5, 2019.

*Primary Examiner* — Scott J Medway
*Assistant Examiner* — Anh Bui
(74) *Attorney, Agent, or Firm* — Stephen J. Kenny; Emily H. Yasharpour; Foley Hoag LLP

(57) ABSTRACT

The present invention relates to a valve component for a medical valve assembly (10), the valve component comprising a deformable body (1) for location in a valve assembly housing, the deformable body comprising a conduit for receiving one or more medical instruments there-through, one or more helical grooves (9) being formed on a surface of the conduit, the one or more helical grooves extending into the deformable body from the conduit surface.

16 Claims, 5 Drawing Sheets

(58) Field of Classification Search
CPC ...... A61M 36/0606; A61M 2039/0646; A61M 39/06; A61M 2039/0633; A61M 2039/262; A61M 2039/267; A61M 2039/066; A61M 2039/064
See application file for complete search history.

(56) References Cited

U.S. PATENT DOCUMENTS

| | | | | |
|---|---|---|---|---|
| 5,620,427 | A * | 4/1997 | Werschmidt | A61M 39/1011 137/516.13 |
| 6,142,981 | A * | 11/2000 | Heck | A61M 39/0606 604/256 |
| 2005/0151105 | A1 * | 7/2005 | Ryan | A61M 39/26 251/149.6 |
| 2007/0173940 | A1 * | 7/2007 | Hestad | A61F 2/44 623/17.12 |
| 2010/0152679 | A1 * | 6/2010 | Tezel | A61M 5/347 604/241 |
| 2021/0299424 | A1 | 9/2021 | King | |

FOREIGN PATENT DOCUMENTS

| | | | |
|---|---|---|---|
| JP | 2015023987 | A | 2/2015 |
| WO | 9422357 | A2 | 10/1994 |
| WO | 2019090351 | A2 | 5/2019 |

* cited by examiner

VALVE COMPONENT AND VALVE ASSEMBLY

CROSS REFERENCE TO RELATED APPLICATIONS

This application is a National Stage filing under section 371 of International Application No. PCT/GB2019/052130, filed on Jul. 30, 2019 and published on Feb. 6, 2020 as WO2020/025945, and claims priority to Great Britain Patent Application No. 1812367.9, filed on Jul. 30, 2018. The entire disclosures of each of the prior applications are hereby incorporated by reference herein.

FIELD OF THE INVENTION

The present invention relates to a valve component and a valve assembly for use in medical applications, and more particularly to a haemostatic valve assembly for use in medical procedures with vascular introducer sheaths, catheters and the like.

BACKGROUND

In this connection, haemostatic valves are used to prevent fluid from inadvertently leaving or entering a body target site, and generally comprise a housing defining a passage there-through adapted to receive an elongated medical instrument such as a catheter in a haemostatic sealed condition.

Valves of this nature are used in a wide variety of surgical procedures and such procedures are becoming increasingly complex, including multiple exchanges of guidewires, catheters, and delivery systems.

Current haemostatic valves generally fall into two basic categories: passive and active. To form the desired fluid tight seal, a passive valve generally relies on a resilient sealing body being deformed by the medical instrument as it is inserted through the valve. An active valve in contrast includes a means requiring activation by a user, typically a surgeon, to move a sealing body into contact with the traversing medical instrument in question.

A wide variety of passive haemostatic valves have been proposed in the past and a common issue with these is that in order to achieve a reliable seal that will continue to seal without leakage despite such multiple exchanges, the entry force and friction to movement on entry and exit of the catheter becomes excessive, potentially damaging the instruments being used, and causing injury to the patient.

Active valves deal with this issue by including mechanisms by which the tightness of the sealing components can be relaxed on entry and exit. Such valves have the disadvantage though that they are more complicated and expensive to manufacture and require an extra operational step for the medical staff to perform, this slowing down the procedure and requiring additional expertise.

An object of the present invention is to alleviate problems associated with known valves.

SUMMARY OF THE INVENTION

According to the present invention there is provided a valve component for a medical valve assembly, the valve component comprising: a deformable body for location in a valve assembly housing, the deformable body comprising a conduit for receiving one or more medical instruments there-through, one or more helical grooves being formed on a surface of the conduit, the one or more helical grooves extending into the deformable body from the conduit surface. In this way, the valve component affords a more reliable sealing arrangement with relatively low insertion forces for medical instruments used therewith.

Preferably, the conduit extends from a proximal end of the body to a distal end of the body, the one or more helical grooves extending into said deformable body from the conduit surface to define one or more helical contact surfaces for contacting one or more medical instruments located in the conduit. In use, such helical contact surfaces are biased into contact with the one or more medical instruments located in the conduit. The inclination of the helical grooves around the axis of the conduit is such as to lead to closure of voids in the grooves on a longitudinal compression resulting from insertion of the one or more medical instruments. This enhances the sealing of the flow path within the deformable body.

Conveniently, a plurality of helical grooves is provided on the conduit surface. Preferably, three helical grooves are provided on the conduit surface. The provision of three grooves has been found to show particularly enhanced sealing properties.

DETAILED DESCRIPTION

In preferred embodiments, the deformable material has a shore hardness 'A' of 5 to 20. Such a shore hardness parameter offers a beneficial degree of resilience.

Preferably, the valve component is for use in a haemostatic valve.

Conveniently, the pitch of one or more of said one or more helical grooves is in the range 2 to 10 mm. Such a pitch affords enhanced sealing properties.

The helical vane diameter of the one or more helical grooves is preferably in the range 2 to 10 mm. Such a vane diameter provides enhanced sealing properties and allows ease of access through the conduit.

According to a further aspect of the present invention there is provided a valve assembly comprising a valve component as defined above, further comprising a valve assembly housing, wherein the housing is adapted to put the deformable body into a compressed state. Simple oversizing of the deformable body with respect to the housing sets up a suitable bias within the body to close voids and prevent leakage.

Preferably, the deformable body has outer dimensions oversized by 1 to 15% in relation to the internal body retaining dimensions of the housing. Conveniently, the body and housing are each cylindrical, with the external diameter of the body being 1 to 15% greater than the internal diameter of the housing.

The deformable body may be a first deformable body, a second deformable body being provided having a conduit for receiving said one or more medical instruments there-though, the conduits of the first and second deformable bodies having a common axis. The second deformable body acts to further enhance sealing of the assembly and assist in guiding the one or more medical instruments into the first deformable body.

Preferably, the conduit of the second deformable body has a widened opening at an introduction end for facilitating introduction of said one or more medical instruments. The opening may have tapered sides and may, for example, have a bowl-like guide surface for assisting the user in readily and reliably introducing one or more medical instruments into the valve assembly.

Conveniently, the first and second deformable bodies abut one other within the housing, with their conduits aligned along a common axis.

Preferably, the walls of the valve assembly housing and/or the first deformable body are tapered to allow variable compression of the deformable body on movement of the deformable body within the housing. In this manner, the sealing properties can be refined if required.

Conveniently, the valve assembly further comprises a purse string suture for opening and closing the valve. As such, the sealing properties of the deformable body can be manipulated if required.

FIGURES

Certain preferred embodiments of the present invention will now be described by way of example and with reference to FIGS. 1 to 8 of the drawings, of which:—

DETAILED DESCRIPTION OF THE FIGURES

The present invention relates to valves for use in medical applications and more particularly to haemostatic valves used in endovascular procedures.

Figure 1:
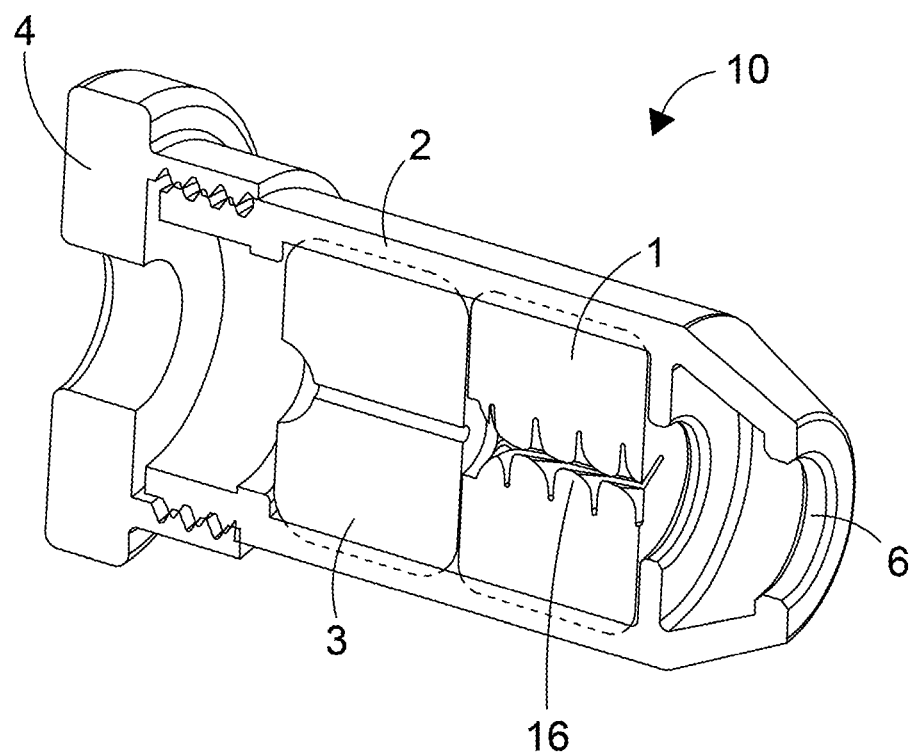
FIG. 1 shows in a sectional view of a valve assembly having a valve component of the present invention.
Figure 2:
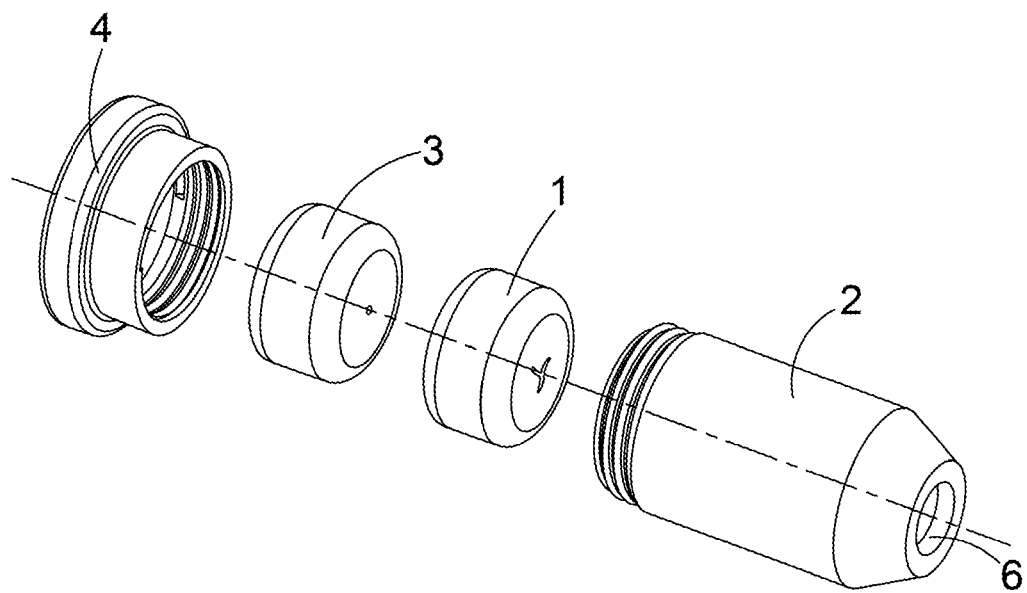
FIG. 2 shows an exploded view of the valve assembly components of FIG. 1.
Figure 3:
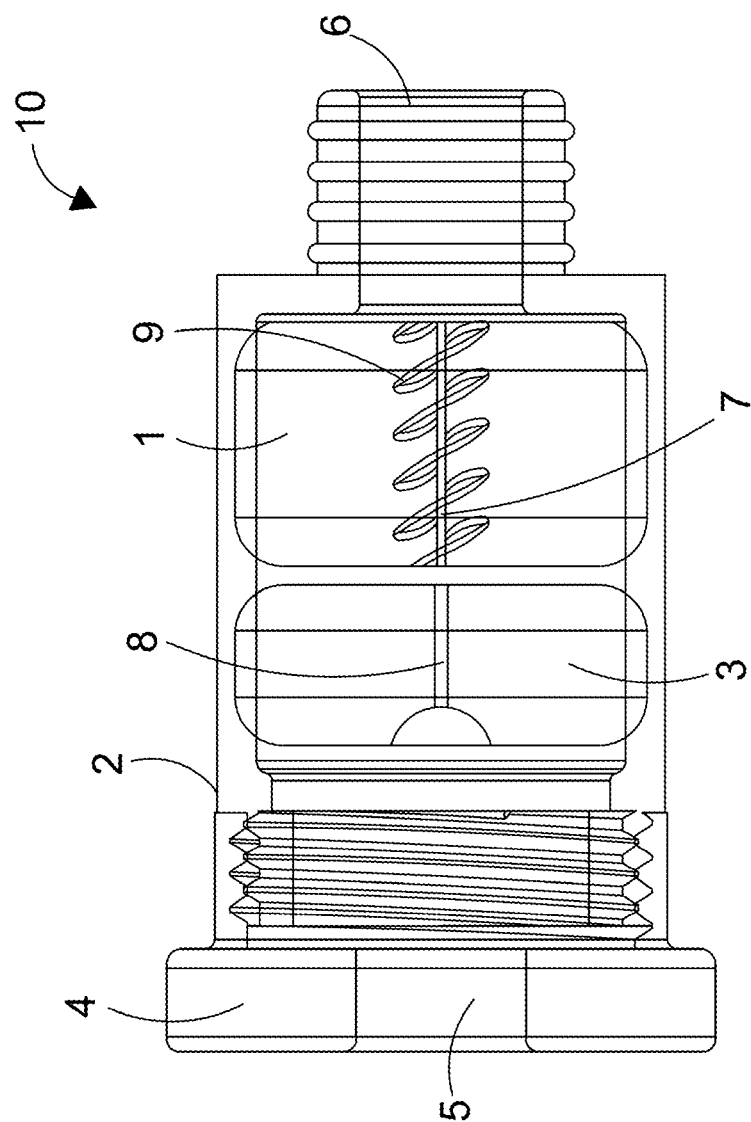
FIG. 3 shows a part cross-sectional view of the valve assembly of FIGS. 1 and 2.

In this connection and as shown in FIGS. 1 to 3, the invention concerns a first deformable body 1 retained within a housing 2 that also preferably houses a second deformable body 3. The first and second deformable bodies may be oversized with respect to the housing so that when inserted within the housing they are in a state of compression. In this regard, the housing comprises a cylindrical body section for retaining the first and second deformable bodies, the diameters of the bodies being oversized by 1 to 15% with regard to the diameter of the cylindrical body section. The deformable bodies are formed of liquid moulded silicon, although any suitable alternative compliant materials, such as rubber, may be used.

An end cap 4 threadingly engages an open end of the housing 2 to close off the assembly 10 formed by the housing, deformable bodies and end cap.

The end cap 4 has an aperture 5 allowing access of one or more medical instruments, such as a catheter (not shown) into the housing. An opposite end of the housing has a similar opening 6 allowing the one or more medical instruments to pass through the assembly, into for example an introducer sheath mounted at this end of the housing.

As shown in FIG. 3, the two deformable bodies 1, 3 each have a preformed conduit 7, 8, the conduits being aligned with the axis passing through apertures 5, 6. The conduits 7, 8 have a cross-section that is dimensioned to be slightly undersized with respect to the cross-section of the medical instrument to be used with the assembly so that the deformable bodies seal around the one or more medical instruments when pushed through the assembly. A typical needle valve might have a diameter of 1.2 mm such that the conduit diameter would be marginally less. Of course, the dimensions of the valve components may be varied to suit the requirements of the instruments with which they are being used.

The first deformable body 1 has one or more helical grooves 9 formed in the conduit surface defining helical contact surfaces 16 for engaging longitudinally along the one or more medical instruments passing through the assembly. The one or more helical grooves are preformed into the material of the first deformable body. The one or more helical grooves may have a helical vane diameter in the range of 2 to 10 mm. In certain preferred embodiments, the one or more helical grooves extend to a diameter of up to 6 mm or more preferably 5.6 mm about the central axis of the conduit through the deformable body. The one or more helical grooves moreover extend longitudinally along a major portion of the first deformable body.

Figure 6:
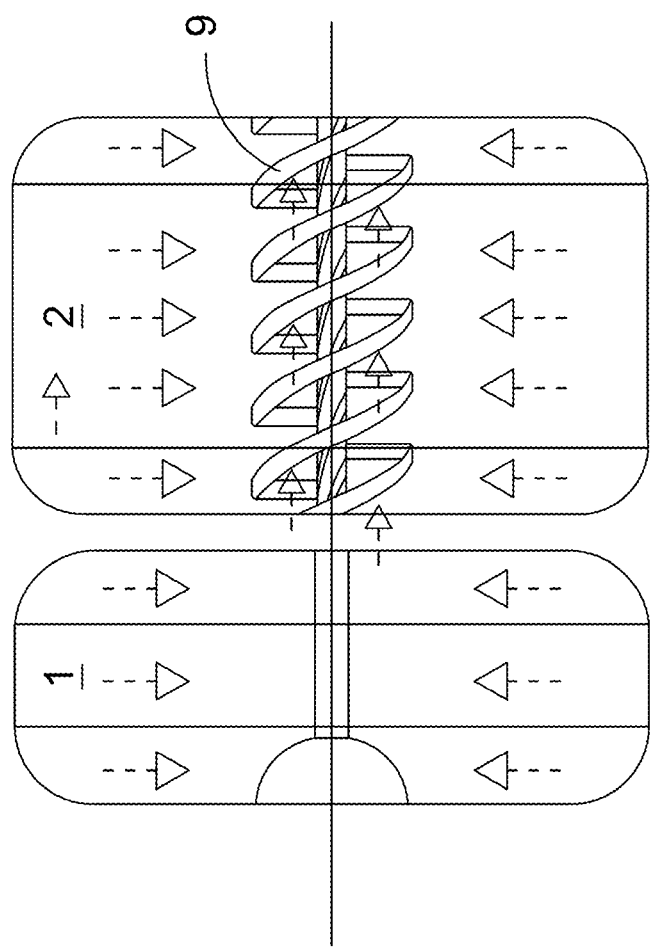
FIG. 6 shows a schematic view of the forces at play on insertion of one or more medical instruments with the valve component of the present invention.

As shown in FIG. 6, the inclination resulting from the helix configuration of the one or more grooves 9 means that on insertion of the one or more medical instruments, a longitudinal compression is applied to the first deformable body 1, which causes helical voids and gaps to close, therefore sealing the flow path through the valve assembly.

In this regard, the pitch of the helical grooves is preferably in the range of 2 to 10 mm, and more preferably 3 mm.

In certain preferred embodiments, the helical vane diameter is in the range 2 to 10 mm and more preferably 5.6 mm.

Figure 4:
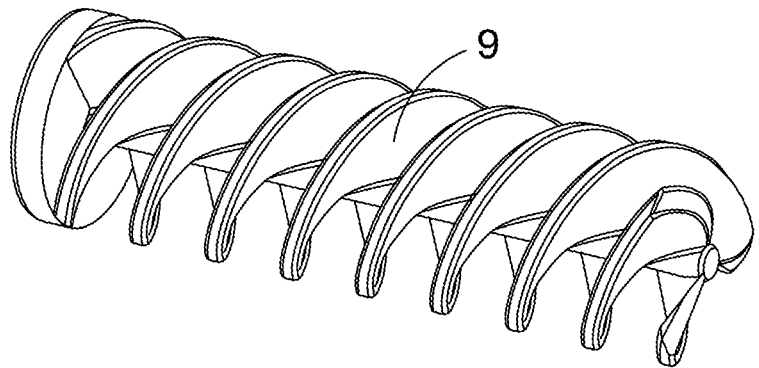
FIG. 4 shows a perspective view of a triple helix core corresponding to triple helix grooves provided around a conduit in a deformable body of the present invention of FIGS. 1 to 3.
Figure 5A:
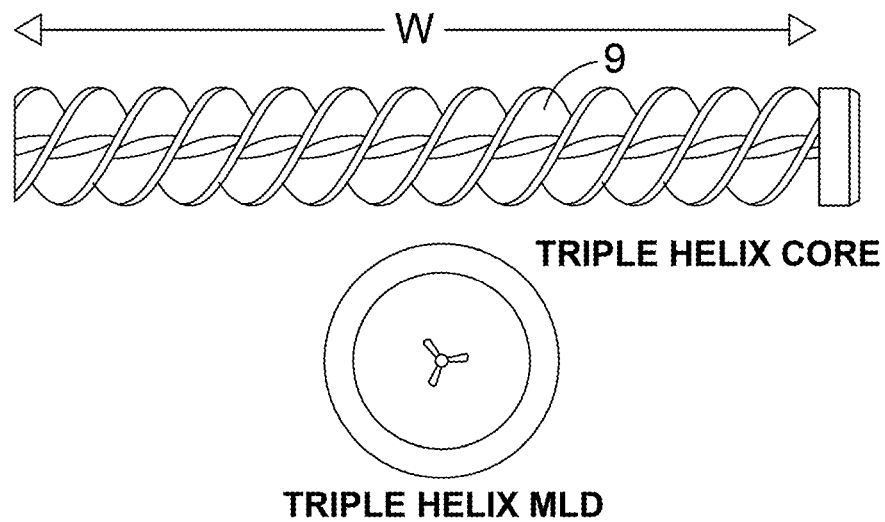
FIGS. 5A, 5B and 5C show single, double and triple helix variants of the present invention.

In the preferred embodiments, three helical grooves are provided, as shown in FIGS. 4 and 5A. Each of said grooves preferably has a helical vane diameter in the range of 2 to 10 mm and preferably 5.6 mm and a pitch in the range of 2 to 10 mm and preferably 3 mm.

Figure 5B:
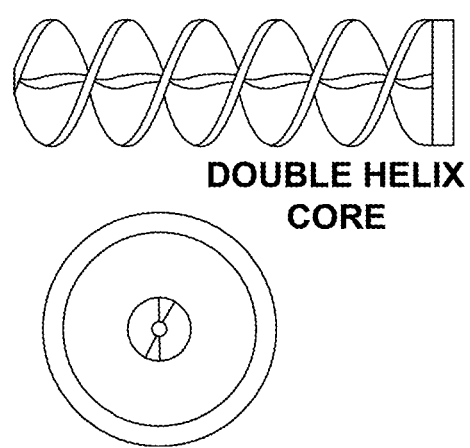
Figure 5C:
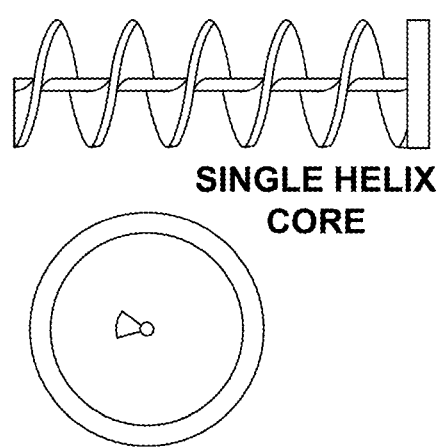

FIGS. 5A, 5B and 5C in this respect show triple, double and single helix variants.

The one or more helical grooves may have a width of 0.8 mm to 2.0 mm.

It is intended that one size of the valve assembly can offer sealing from wire entry up to a 23Fr OD Anaconda® delivery sheath.

Figure 7:
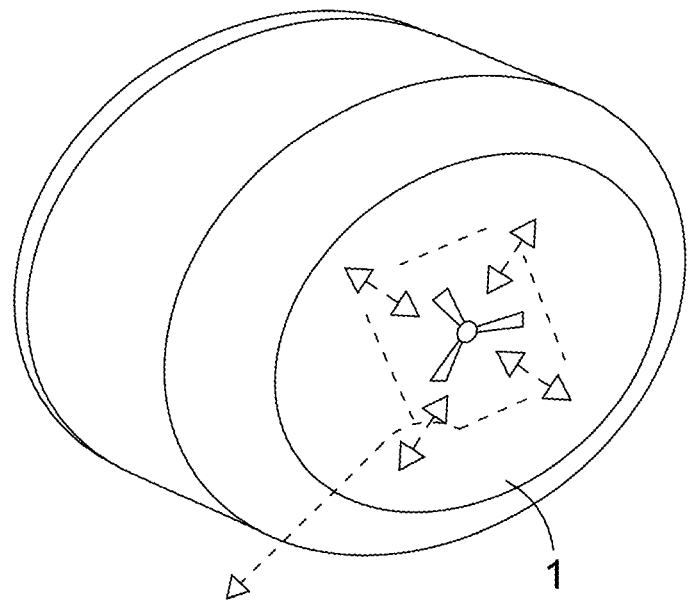
FIG. 7 shows a variant of a valve assembly having a valve component according to a further embodiment of the present invention.

Whilst the above described valve assembly incorporates a passive valve component, in certain circumstances, it may be necessary to refine the sealing properties of the assembly, for example for a surgeon to control back flow leakage. FIG. 7 shows a variant of a valve component according to a further embodiment of the present invention where the deformable body 1 has a purse string sealing arrangement to enable refinement of the sealing properties of the assembly.

Figure 8:
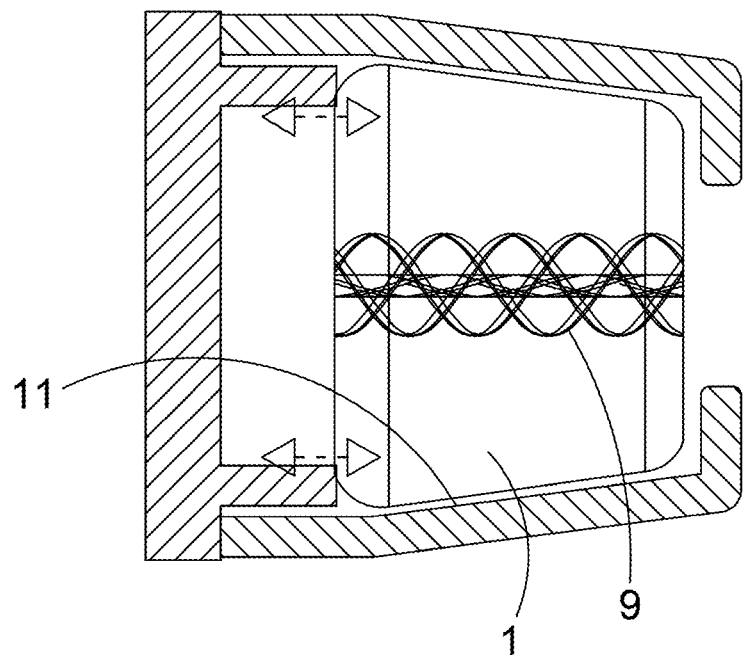
FIG. 8 shows a variant of a tapered valve body according to a further embodiment of the present invention.

FIG. 8 shows a further variant of a valve assembly where the inward facing walls 11 of the housing are tapered, as are the outer surface walls of the first deformable body 1. In this way, by moving the first deformable body relative to the walls 11, the strength of compression of the deformable body 1 can be increased and decreased, thereby varying the sealing properties of the assembly.

In preferred embodiments, the enhanced sealing properties afforded by the valve assembly allow it to accommodate multiple catheter insertions simultaneously.

The invention claimed is:

1. A valve component for a medical valve assembly, the valve component comprising:
   a first deformable body for location in a valve assembly housing, the first deformable body comprising a first conduit for receiving one or more medical instruments there-through,
   a second deformable body for location in the valve assembly housing, the second deformable body comprising a second conduit having a first end and a second end for receiving the one or more medical instruments there through, the first conduit being aligned with the second conduit,
   one or more helical grooves being formed on an interior surface of the first conduit, the one or more helical grooves extending longitudinally from a first end to the second end of the first conduit with a first helical groove of the one or more helical grooves spaced from an adjacent helical groove of the one or more helical grooves into the first deformable body from the interior surface of the first conduit when the first deformable body is in an uncompressed state, and
   wherein in a compressed state a helical void of the one or more helical grooves closes to seal a flow path through the valve assembly housing.

2. The valve component of claim 1, wherein the first conduit extends from a proximal end of the first deformable body to a distal end of the first deformable body, the one or more helical grooves extending into said first deformable body from the interior surface of the first conduit to define one or more helical contact surfaces for contacting the one or more medical instruments located in the first conduit.

3. The valve component of claim 1, wherein the one or more helical grooves comprise a plurality of helical grooves provided on the interior surface of the first conduit.

4. The valve component of claim 1, wherein the one or more helical grooves comprise three helical grooves provided on the interior surface of the first conduit.

5. The valve component of claim 1, wherein the first deformable body comprises a material having a shore hardness 'A' of 5 to 20.

6. The valve component of claim 1, wherein the valve component is for use in a haemostatic valve.

7. The valve component of claim 1, wherein a pitch of one or more of said one or more helical grooves is in the range of 2 to 10 mm.

8. The valve component of claim 1, wherein a helical vane diameter of the one or more helical grooves is in the range of 2 to 10 mm.

9. The valve component of claim 1, further comprising the valve assembly housing, wherein the valve assembly housing is adapted to put the first deformable body into a compressed state.

10. The valve component of claim 9, wherein the first deformable body has outer dimensions oversized by 1 to 15% in relation to the valve assembly housing.

11. The valve component of claim 9, wherein the first deformable body and the valve assembly housing are each cylindrical, with an external diameter of the first deformable body being 1 to 15% greater than that of the internal diameter of the valve assembly housing.

12. The valve component of claim 1, wherein the second conduit of the second deformable body has a widened opening at an introduction end for enhancing introduction of said one or more medical instruments.

13. The valve component of claim 1, wherein the second conduit of the second deformable body has a tapered opening at an introduction end for enhancing introduction of said one or more medical instruments.

14. The valve component of claim 1, wherein, the first and second deformable bodies abut one other within the valve assembly housing, with the first and second conduit aligned.

15. The valve component of claim 9, wherein walls of the valve assembly housing and/or the first deformable body are tapered to allow variable compression of the first deformable body or movement of the first deformable body within the valve assembly housing.

16. The valve component of claim 9, further comprising a string suture for opening and closing the valve component.

* * * * *